United States Patent
Sumiya et al.

[19]

[11] Patent Number: 5,906,608
[45] Date of Patent: May 25, 1999

[54] ABLATION APPARATUS

[75] Inventors: Toshifumi Sumiya, Nukata-gun; Takashi Hagiwara, Gamagori, both of Japan

[73] Assignee: Nidek Co., Ltd., Gamagori, Japan

[21] Appl. No.: 09/013,884

[22] Filed: Jan. 27, 1998

Related U.S. Application Data

[63] Continuation-in-part of application No. 08/782,282, Jan. 13, 1997.

[30] Foreign Application Priority Data

Jan. 31, 1996 [JP] Japan .................................. 8-038975
Jan. 31, 1997 [JP] Japan .................................. 9-033346

[51] Int. Cl.$^6$ .................................................. A61N 5/06
[52] U.S. Cl. .................................................. 606/5; 606/4
[58] Field of Search .................................. 606/4–6, 10

[56] References Cited

U.S. PATENT DOCUMENTS

| | | |
|---|---|---|
| 4,665,913 | 5/1987 | L'Esperance, Jr. . |
| 4,941,093 | 7/1990 | Marshall et al. . |
| 5,144,630 | 9/1992 | Lin . |
| 5,376,086 | 12/1994 | Khoobehi et al. . |
| 5,395,356 | 3/1995 | King et al. .................................. 606/4 |
| 5,507,799 | 4/1996 | Sumiya . |
| 5,520,679 | 5/1996 | Lin . |
| 5,569,238 | 10/1996 | Shei .................................. 606/4 |
| 5,624,436 | 4/1997 | Nakamura et al. .................................. 606/12 |
| 5,713,892 | 2/1998 | Shimmick .................................. 606/5 |

FOREIGN PATENT DOCUMENTS

| | | |
|---|---|---|
| A-4-242644 | 8/1992 | Japan . |
| A-6-166231 | 6/1994 | Japan . |

*Primary Examiner*—Beverly M. Flanagan
*Assistant Examiner*—Roy Gibson
*Attorney, Agent, or Firm*—Oliff & Berridge, PLC

[57] ABSTRACT

An ablation apparatus for ablating only a convex part on a rough surface efficiently in a short time, providing a light delivering optical system for delivering a laser beam being a slender from a laser beam source rectangular shape to an object to be ablated, a beam moving device for moving the laser beam to an intersecting direction relative to the optical axis of the light delivering optical system, a dividing-and-masking device for dividing selectively a longer-side direction of the laser beam of which a cross section is a rectangular shape and masking the same selectively, a data input device for inputting data relating to an ablation area of the object, and a control device for controlling the condition masked by the dividing-and-masking device at respective positions of the laser beam moved by the beam moving device based on the data inputted by using the data input device, wherein convex parts of the object of which a surface being roughness is ablated by the laser beam through the dividing-and-masking device and the beam moving device.

19 Claims, 6 Drawing Sheets

LASER BEAM

ABLATION APPARATUS

This is a Continuation-in-Part of application Ser. No. 08/782,282 filed Jan. 13, 1997. The entire disclosure of the prior application is hereby incorporated by reference herein in its entirety.

BACKGROUND OF THE INVENTION

1. Field of the Invention

The present invention relates to an ablation apparatus for ablating a convex part on a rough surface of an object, and more particularly to the ablation apparatus suitable for correcting roughness on the surface of a cornea by ablating selectively only the convex part on the surface of the cornea having irregular astigmatism and the like.

2. Description of Related Art

Recently it is known in general that PRK (Photorefractive Keratectomy) is utilized for correcting an ametropia of an eye by ablating the surface of the cornea by a laser beam and by changing its curvature, and PTK (Phototheraputic Keratectomy) is applied for removing a diseased portion on the surface of the cornea by ablating with the laser beam. The ablation by the laser beam for performing the PRK and PTK has been carried out by the following three methods.

The first method is to ablate a predetermined area by a laser beam having large area all at once, the second method is to ablate a predetermined area by moving a rectangular laser beam, and the third method is to ablate a predetermined area by making it scan a small spot in a two-dimensional way.

However, the human cornea is not always like a spherical surface or toric surface, but the surface of the cornea happen to be roughness partially due to the irregular astigmatism and the like. When it is try to make the surface of the cornea to be a spherical surface or a toric surface by ablating with a laser beam, in the case of the first method that applies a beam having large area or the second method that moves the rectangular laser beam, since each convex part had to be ablated one by one in a manner that adjusting an irradiation area to the convex part, it results in such disadvantage that it takes much more time.

On the other hand, in the case of the third method that scans a small spot, convex parts can be ablated in less time compared with the first and the second methods, the ablation is carried out by scanning and ablating selectively only the convex part. However if there are many convex parts to be ablated, it also results in such disadvantage that it takes relatively much time.

SUMMARY OF THE INVENTION

The present invention has been made in view of the above circumstances and has an object to overcome the above problems and to provide an ablation apparatus, capable of ablating only a convex part on the rough surface efficiently in a short time.

The another object of the invention is to provide an ablation apparatus, capable of ablating a convex part on the rough surface smoothly.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ablation apparatus comprises light delivering optical system for delivering a laser beam of which a cross section at a perpendicular plane relative to an optical axis is a slender rectangular shape to an object to be ablated, beam moving means for moving the laser beam to an intersecting direction relative to the optical axis of the light delivering optical system, dividing-and-masking means for dividing selectively a longer-side direction of the laser beam of which a cross section is a rectangular shape and masking the same selectively, data input means for inputting data relating to an ablation area of the object, and control means for controlling the condition masked by the dividing-and-masking means at respective positions of the laser beam moved by the beam moving means and the position moved by the deviding mask moving means based on the data inputted by using the data input means, whereby convex parts of the object of which a surface is roughness are ablated by the laser beam that is delivered through the light delivering optical system.

In another aspect of the present invention, the ablation apparatus comprises light delivering optical system for delivering a laser beam of which a cross section at a perpendicular plane relative to an optical axis is a slender rectangular shape to an object to be ablated, beam moving means for moving the laser beam to an intersecting direction relative to the optical axis of the light delivering optical system, dividing-and-masking means for dividing selectively a longer-side direction of the laser beam of which a cross section is a rectangular shape and masking the same selectively, divided mask moving means for moving the dividing-and-masking means along the longer-side direction of the laser beam, data input means for inputting data relating to an ablation area of said object, and control means for controlling the condition masked by the dividing-and-masking means at respective positions of the laser beam moved by the beam moving means and the position moved by the deviding mask moving means based on the data inputted by using the data input means, whereby convex parts of the object of which a surface being roughness are ablated by the laser beam that is delivered through the light delivering optical system.

In another aspect of the present invention, the ablation apparatus comprises light delivering optical system for delivering such a laser beam of which a cross section is a slender rectangular shape that has an approximate uniform intensity distribution of the beam in one direction, and a Gaussian distribution in another direction, to an object to be ablated, beam moving means for moving the laser beam to the direction of Gaussian distribution of the beam relative to the optical axis of the light delivering optical system, dividing-and-masking means for dividing selectively a longer-side direction of the laser beam of which a cross section is a rectangular shape and masking the same selectively, data input means for inputting data relating to an ablation area of the object, and control means for controlling the condition masked by the dividing-and-masking means at respective positions of the laser beam moved by the beam moving means based on the data inputted by using the data input means, whereby convex parts of the object of which a surface is roughness are ablated by the laser beam that is delivered through the light delivering optical system.

As described above, according to the present invention, the apparatus enables to ablate convex parts on an roughness surface of an object efficiently in a short time and smoothly.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawing.

DETAILED DESCRIPTION OF THE PREFERRED EMBODIMENTS

Figure 1:
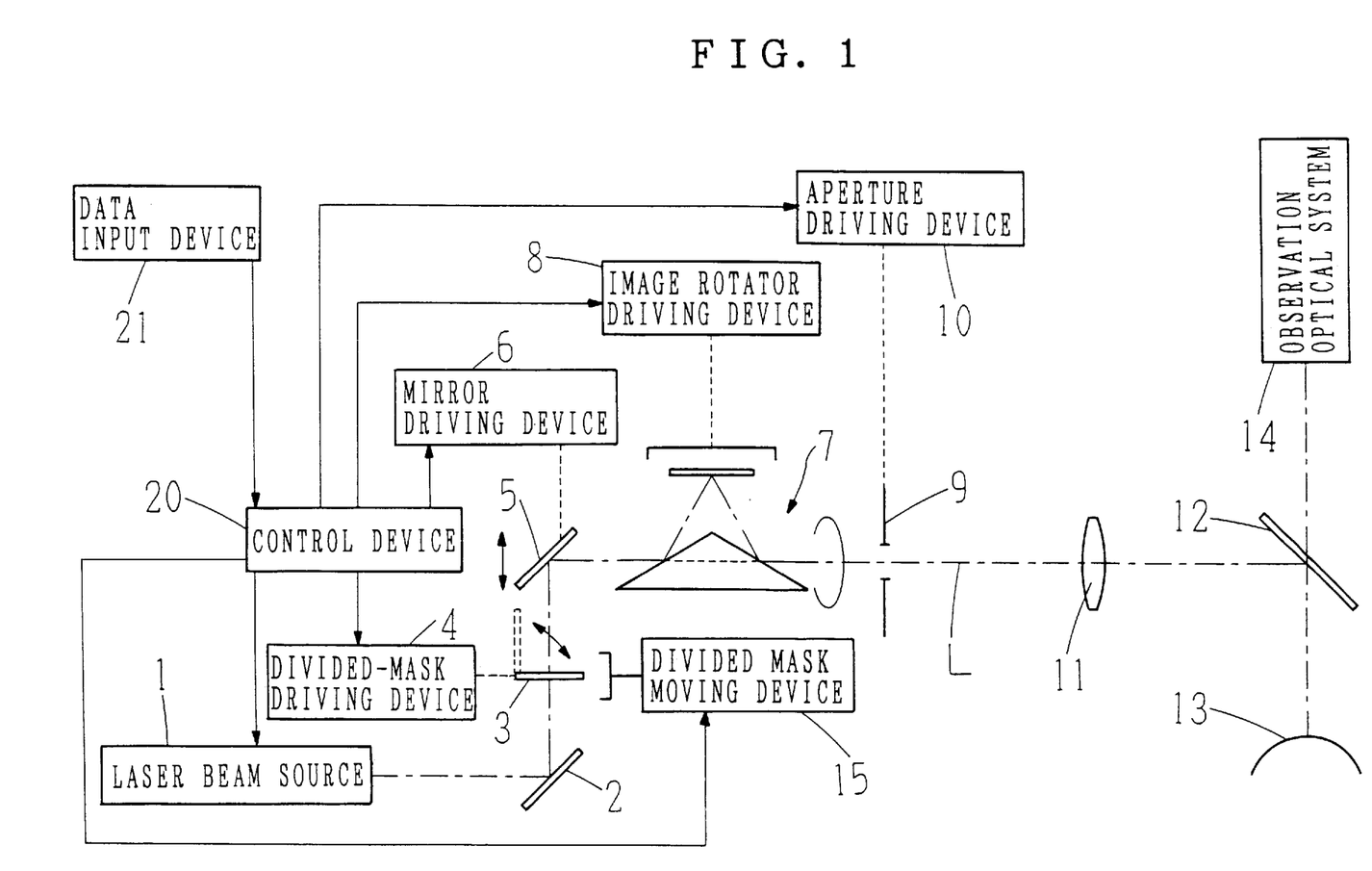
FIG. 1 is a block diagram showing a schematic arrangement of an optical system and a schematic construction of a control system of the preferred embodiment.

A detailed description of one preferred embodiment of an ablation apparatus embodying the present invention will now be given referring to the accompanying drawings. FIG. 1 is a block diagram showing a schematic arrangement of an optical system and a schematic construction of a control system of the preferred embodiment.

Figure 2:
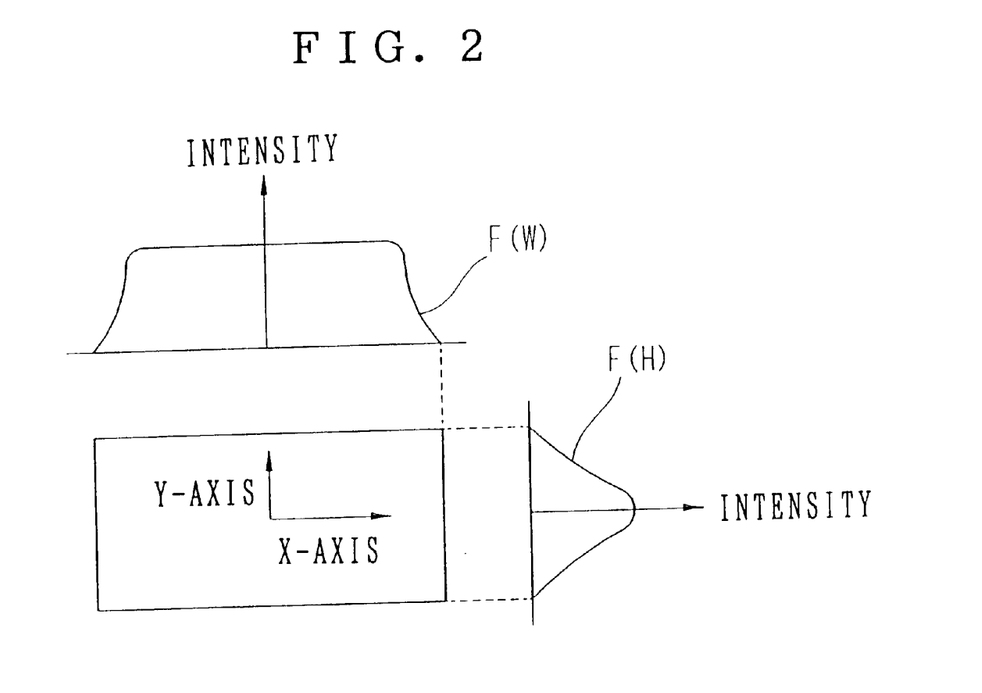
FIG. 2 is a view showing a typical shape of excimer laser beam.

Reference numeral 1 is a laser beam source, and an excimer laser source with a wavelength of 193 nm is used in the preferred embodiment. The excimer laser beam emitted from the laser beam source 1 is a pulse wave, referring to FIG. 2 which shows its typical shape, an intensity distribution has an approximate uniform distribution F(W) in the horizontal direction (X-axis direction) and a Gaussian distribution F(H) in the perpendicular direction (Y-axis direction). Also, its cross section at the perpendicular plane relative to an optical axis is a slender rectangular shape.

The laser beam emitted from the laser beam source 1 is formed into a desired rectangular shape by a beam forming means such as an expander lens and the like as the occasion demands. Reference numeral 2 is a plane mirror for deflecting the laser beam at 90° upward, that is emitted from the laser beam source 1 to a horizontal direction.

Figure 3:
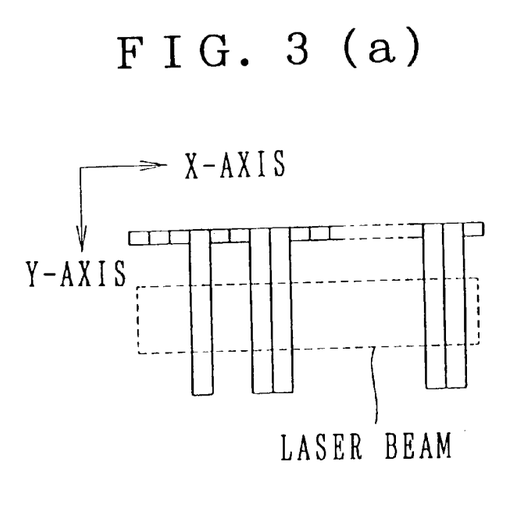
FIGS. 3(a) and 3(b) are views for explaining a shape and an opening and shutting mechanism for divided masks.
Figure 4A:
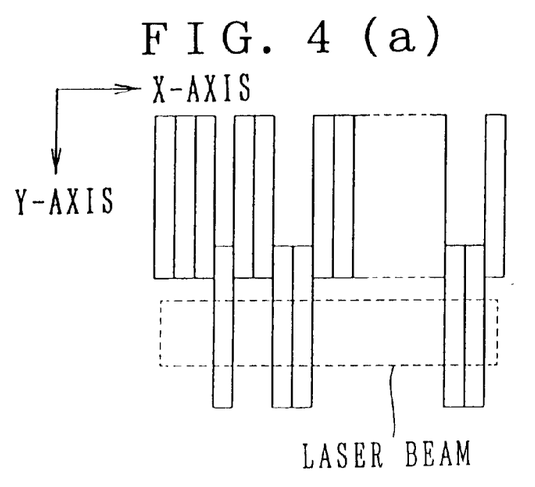
FIGS. 4(a) and 4(b) are views for explaining another opening and shutting mechanism for divided masks.
Figure 4B:
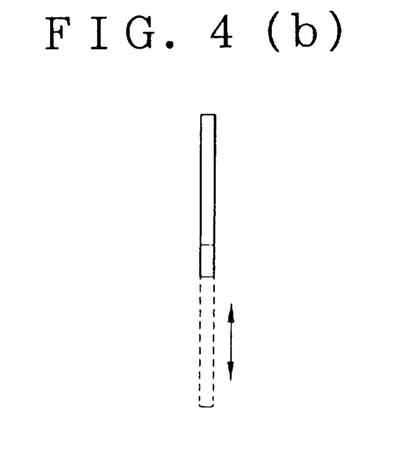

Reference numeral 3 is a divided mask for dividing the laser beam in a horizontal direction (X-axis direction) and intercepting the divided laser beam partially, and the parts to be intercepted are changed selectively by a divided-mask driving device 4. As viewing the divided mask 3 from the laser beam source side, as shown in FIG. 3(a), there is a form that many strip-shaped masks having approximately the same width are arranged, and by opening and shutting these strip-shaped masks respectively, longer-side direction(X-axis direction) of the slender rectangular laser beam can be cut off partially. Regarding the opening/shutting for each strip-shaped mask, as shown FIG. 3(b), each strip-shaped mask is rotated by the rotating mechanism, so that the intercepted parts can be changed selectively. That is, the laser beam passing through the divided mask 3 comes to be such a shape that the shut parts of the mask are partially cut by opening and shutting each strip-shaped mask selectively. Furthermore, the opening and shutting operation for the strip-shaped masks are performed by rotating them as well as sliding the masks in a perpendicular direction of the laser beam as shown in FIG. 4(a) and FIG. 4(b).

Also, the divided mask 3 is moved along the longer-side direction(X-axis direction) of the laser beam by a divided-mask moving device 15. The moving range is secured at least the width of one strip-shaped mask, and the whole of the divided mask 3 is configured so as to move minute distance less than the width of the mask.

The laser beam passing through the divided mask 3 is changed to a horizontal direction by a plane mirror 5. The plane mirror 5 can be moved in a perpendicular direction (the direction denoted by an allow) by a mirror driving device 6, and the laser beam is moved parallel along the direction of Gaussian distribution so as to ablate an object uniformly. Since the detail concerning this point is mentioned in Japanese Laid-open NO.HEI 4(1992)-242644 (the title of the invention "ABLATION APPARATUS FOR ABLATING AN OBJECT BY LASER BEAM" (corresponding to U.S. Pat. Ser. No. 5,507,799)), it is cited.

Reference numeral 7 is an image rotator which is driven so as to rotate on an optical axis L by an image rotator driving device 8 to make the laser beam rotate on the optical axis. Reference numeral 9 is a variable circular aperture for restricting an ablation area, and the aperture diameter of the aperture 9 is varied by an aperture driving device 10. Reference numeral 11 is a projection lens for use in projecting the aperture 9 onto a cornea 13 of a patient's eye. As the aperture 9 and the cornea 13 are conjugate positional relationship relative to the projection lens 11, the area restricted by the aperture 9 is focused on the cornea 13, thereby the ablation area is restricted.

Reference numeral 12 is a dichroic mirror having the characteristic for transmitting a visible light and for reflecting the excimer laser beam of 193 nm. The laser beam through the projection lens 11 is bent by 90° by means of the dichroic mirror 12, so that it may be guided to the cornea 13 of the patient's eye.

In surgery, the patient's eye is aligned in advance so that it can be located at the predetermined position (since an alignment means is less related to the present invention, the detail is omitted herein).

Reference numeral 14 is an observation optical system having a surgical binocular microscope, and is located above the dichroic mirror 12. As the binocular observation optical system, commercial types can be available, so the description is omitted herein since the construction is not concerned with the present invention.

Reference numeral 20 is a control device for controlling the whole of devices including the laser source 1, the divided mask driving device 4, the mirror driving device 6, the image rotator driving device 8, the aperture driving device 10, the divided mask moving device 15 and the like. Reference numeral 21 is a data input device for use in inputting data of the corneal shape of patient's eye and the like.

In respect to the apparatus with above construction, the operation will be described hereinafter.

Firstly, the correction of refraction by using laser beam will be described intelligibly. The cornea of patient's eye is fixed to the predetermined position with respect to the apparatus. The ablation area and its shape are determined in response to the programs stored in the control device 20 based on the data such as refractive power and the like that are inputted by the data input device 21 in advance, thereby operation for the apparatus is controlled. In the case of correction of refraction, all masks of the divided mask 3 are made to be released.

In the case of correction of myopia, the laser beam is restricted by the aperture 9, and then the laser beam is moved to the direction of Gaussian distribution by moving the plane mirror 5 in order. Then, every time when the laser beam has finished moving from one edge to another edge of the plane (that is, one scan), the moving direction of the laser beam is rotated by the image rotator 7 to remove the cornea to be an uniform and circular shape. By varying the size of the aperture 9 in order, the center part of the cornea is ablated deeply, the peripheral part of that is ablated shallowly. Whereby the correction of myopia is performed.

In case of correction of hypermetropia, firstly a diameter of the aperture 9 is fixed to restrict the ablation area. The laser beam is shifted by making the plane mirror 5 move relative to the optical axis L, and the ablation is repeated by rotating the image rotator 7 so that the cornea is ablated to be a ringed shape. If the number of irradiation pulse (irradiation time) is made to be increased in response to displacement due to successive movement of the plane mirror 5 between the optical axis L and the laser beam, then the ablation is performed so that the center part may be shallowly and the peripheral part may be deeply, thereby the correction of hypermetropia is performed. Controlling a corrected power is accomplished by changing the whole number of irradiation pulse without changing the ratio of a number of irradiation pulse (irradiation time) at each position of the laser beam which is shifted from the optical axis L by a movement of the plane mirror 5. The detail of the correction of hypermetropia is mentioned in Japanese Application No.HEI 6(1994)-166231 (the title of the invention "APPARATUS FOR USE IN OPERATING A CORNEA"), which corresponds to U.S. patent application Ser. No. 08/466,430 by an applicant of this invention.

Figure 8:
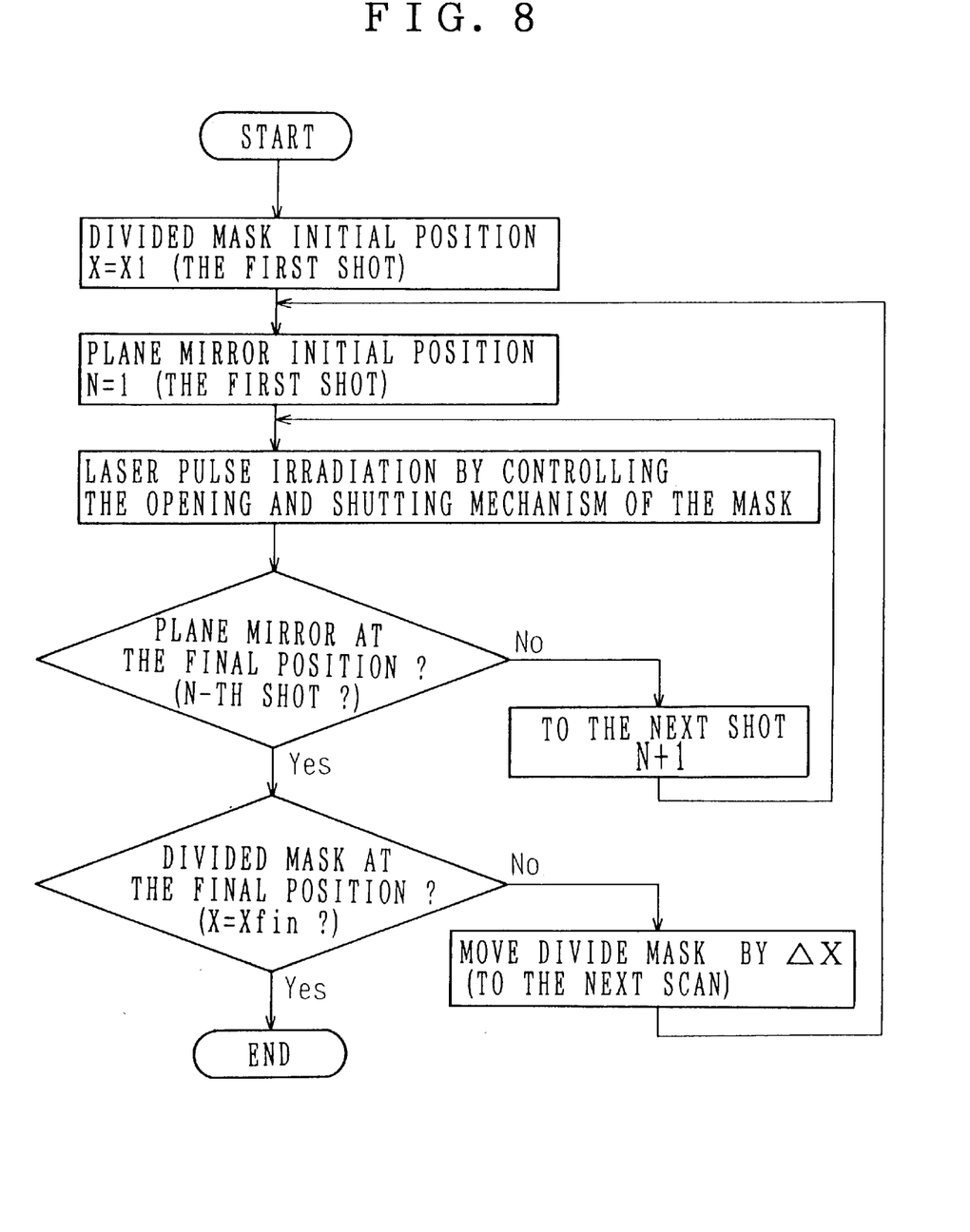
FIG. 8 is a flow chart for explaining such an operation that ablates selectively only convex parts of the cornea having irregular astigmatism or the like in the present invention.

Next, it will be described hereinafter as regards the operation for ablating selectively only convex parts of the cornea having an irregular astigmatism or the like with referring to the flow chart shown in FIG. 8.

Figure 5:
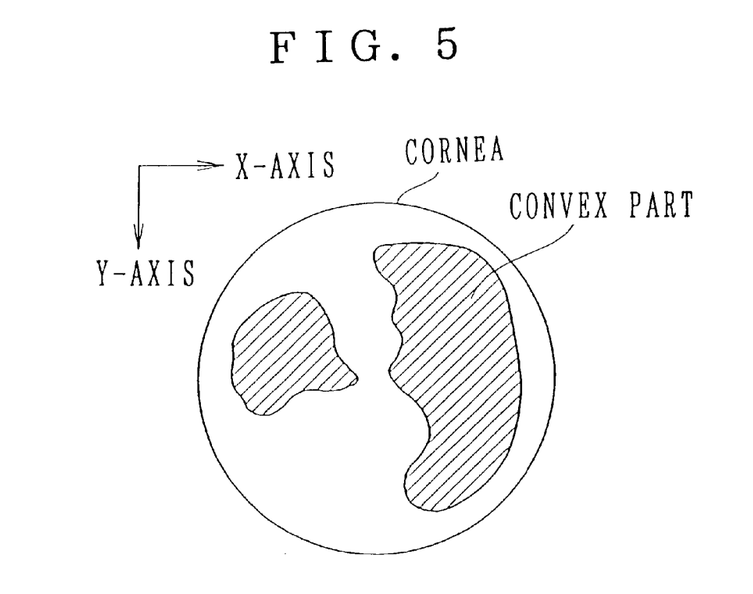
FIG. 5 is a view showing a cornea with convex parts to describe such an operation that removes selectively only convex parts of the cornea.

To begin with, it is assumed that the cornea 13 having convex parts denoted by oblique lines in FIG. 5 is ablated so as to remove the convex parts and to be a spherical surface. In FIG. 5, X-axis and Y-axis show the distribution direction of the laser beam. Firstly, the data of the surface shape of the cornea 13 to be ablated is inputted by the data input device 21. The control device 20 performs the ablation by calculating the ablation amount at each position on the cornea surface and by controlling the moving position of the plane mirror 5 and the opening and shutting mechanism for the strip-shaped masks of the divided mask 3 based on the data of the surface shape as following. Although the plane mirror 5 is moved under the condition synchronized with the laser pulse, it is defined, to make the description clear, that the plane mirror 5 is moved every time when one shot is performed. In this embodiment, although the ablation is performed under the condition that the image rotator 7 is fixed, it may be also performed under the condition that the image rotator 7 is rotated every one scan as occasion demands.

In the first scan, the laser beam is irradiated while the divided mask 3 is arranged to an initial position (the coordinate x is defined as x1). Upon performing the first shot, the plane mirror 5 is positioned at the edge of the cornea. The projected position of the laser beam at the plane mirror 5 is at the edge of the cornea denoted by dotted line shown in FIG. 6(a). However, as there is no convex parts to be ablated in this position, all strip shaped masks of the divided mask 3 are kept shutting by the control device 20. The laser beam emitted from the laser beam source 1 is all cut off by the divided mask 3, therefore the cornea 13 is not ablated.

Figure 6:
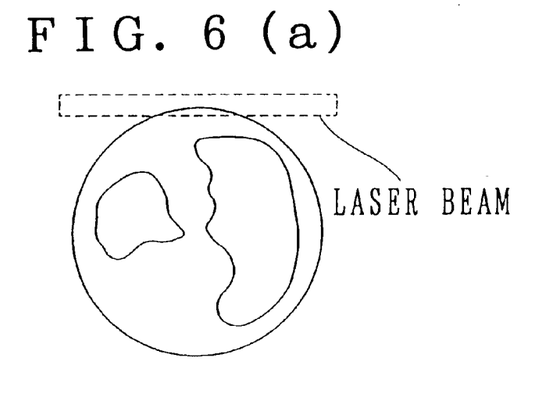
FIGS. 6(a)–6(f) are views for explaining an ablation process for ablating the convex parts of the cornea shown in FIG. 5.

Upon performing the second shot, the plane mirror 5 is moved under the condition synchronized with the laser pulse and moved in a constant distance by the control device 20. Although the projected position of the laser beam at the position is shown in FIG. 6(b), since there is also no convex parts to be ablated, all the divided mask 3 remains shutting. The laser beam is cut off altogether, still, the cornea 13 is not ablated.

Upon performing the third shot, the plane mirror 5 is moved in a constant distance with the same manner. The projected position of the laser beam is at the dotted line shown in FIG. 6(c). Since the convex part to be ablated exists at this position, the divided mask driving device 4 is operated and controlled by the control device 20 based on the data of the shape of the convex parts, so that the strip-shaped parts of the divided masks 3 corresponding to the convex parts may be selectively opened. The laser beam through the opened part of the mask is irradiated onto the cornea 13, so that the convex part denoted by oblique lines in FIG. 6(c) may be ablated.

Upon performing the fourth shot, by the movement of the plane mirror 5, the projected position of the laser beam is located at the position denoted by dotted lines in FIG. 6(d), then mask parts of the divided mask 3 corresponding to the convex part are opened so that the oblique lined part of the cornea 13 is ablated. Upon performing the fifth shot with the same way, the corneal part denoted by oblique lines in FIG. 6(e) is ablated by the movement of the plane mirror 5 and the opening and shutting operation for the mask parts of the divided mask 3 corresponding to the convex part.

When these process is repeated until the n-th shots shown in FIG. 6(f), the plane mirror 5 is made to move to another edge of the opposite side, then the ablation for one scan is completed.

Figure 7:
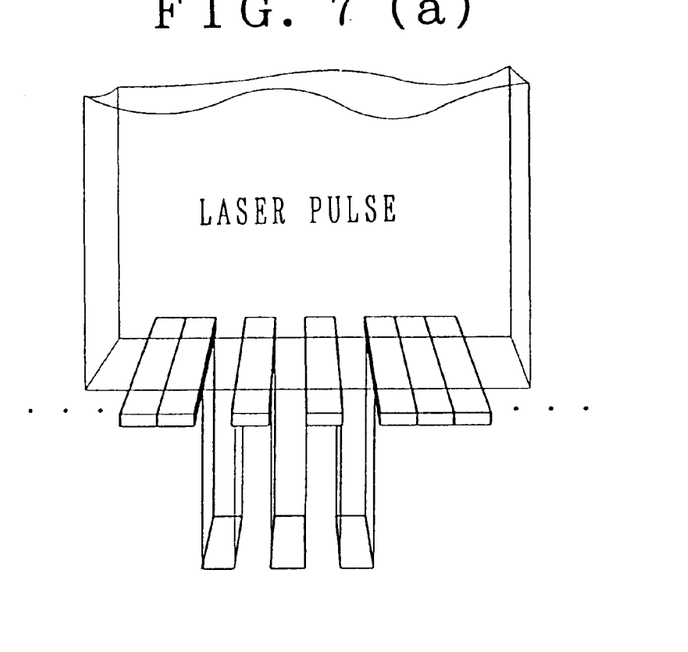
FIGS. 7a–7b are views for explaining a change of an ablation area caused by the movement of divided masks according to the present invention.

Next, the control device 20 makes the divided mask 3 move $\Delta x$ to the longer-side direction(X-axis direction) of the laser beam by the divided mask moving device 15. FIG. 7(a) is a view of explaining the ablation state in case of the first scan, and FIG. 7(b) is a view of explaining the ablation state in case of the second scan that is performed at the same position on the cornea as FIG. 7(a).

After the control device 20 has made the divided mask 3 move to the irradiation position sifted by $\Delta x$ from the position of the first scan by way of the divided mask moving device 15, again, it performs the ablation by controlling the movement of the plane mirror 5, the opening and shutting mechanism for the divided mask 3 and the number of the irradiation pulse (irradiation time) based on the ablation amount at each position obtained by the data that are inputted by the data input device 21 with the same manner mentioned above.

The plane mirror 5 is controlled to move from the ending point to the starting point of the first scan, that is, to the opposite direction to the first scan. Concretely, after the ablation for the first scan is performed from the upper side to the lower side of the cornea in FIG. 5, the ablation for the second scan is performed from the lower side to the upper side. The ablation on and after the third scan is a repetition of these process.

The divided mask 3 is moved $\Delta x$ to X-axis direction on and after the third scan, and it is repeated until the divided mask 3 is moved to a final point (the coordinate x is $X_{fin}$).

The amount of the movement Δx of each scan is not always a constant, and in this case the opening and shutting mechanism of the divided mask 3 and the number of irradiation pulse may be controlled based on the displacement Δx.

As described above, the ablation is carried out based on the data of the shape of the convex part of the cornea 13 while the movement of the laser beam by the plane mirror 5 and the opening and shutting operation for each strip-shaped mask of the divided mask 3 are controlled, and also if it is repeated until the position denoted by oblique lines shown in FIG. 5 has been ablated based on the height information of the convex part, then the convex parts denoted by oblique lined are removed and the cornea 13 is formed to be a spherical surface.

Also, since the divided mask 3 is moved minute distance to the longer-side direction(X-axis direction) of the laser beam, the coordinate of the spot formed by selectively opening masks increases, thereby the ablation area of each scan can be overlapped. In this way, the unevenness which is formed at the position where each mask is divided can be removed, and the ablation surface can be smoothed.

Actually, since the ablation depth at a certain position is found on the basis of the relationship between the intensity of the laser beam per 1 pulse and the number of irradiation pulse, the opening and shutting operation for each strip-shaped mask at the moving position of laser beam and the amount of the movement of the divided mask 3 is determined in accordance with this relationship.

In this embodiment mentioned above, although the control of the ablation is performed by reciprocating movement of the laser beam on the cornea, the ablation of the second scan can be done to the same direction as the first scan (the direction from the upper side to the lower side of the cornea shown in FIG. 5). In this case, the plane mirror 5 may be moved to the initial position every time when each scan has finished, or the movement of the plane mirror 5 may be controlled after only the laser beam is moved to the same position as the initial position (the position shown in FIG. 6(a)) by rotating the image rotator 7 by 180°.

The present invention is not also limited to the embodiment as to the form of the divided mask, and various modifications are possible and they are included in the scope of the present invention as long as they have the same technical ideas as the present invention.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications are suited to the particular use contemplated.

It is intended that the scope of the invention be defined by the claims appended hereto, and their equivalents.

What is claimed is:

1. An ablation apparatus comprising:
   light delivering optical system for delivering a laser beam of which a cross section at a perpendicular plane relative to an optical axis is a slender rectangular shape to an object to be ablated;
   beam moving means for moving the laser beam to an intersecting direction relative to the optical axis of said light delivering optical system;
   dividing-and-masking means for dividing selectively a longer-side direction of the laser beam of which a cross section is a rectangular shape and masking the same selectively;
   data input means for inputting data relating to an ablation area of said object; and
   control means for receiving the data input to said data input means and for controlling the condition masked by said dividing-and-masking means at respective positions of the laser beam moved by said beam moving means based on the data inputted by using said data input means, wherein the ablation apparatus ablates convex parts of the object which have a surface roughness.

2. The ablation apparatus according to claim 1, wherein said dividing-and-masking means consists of a large number of strip-shaped masks arranged in a longer-side direction of the laser beam of which a cross section is a rectangular shape, and
   advancing-and-retracting means for advancing said strip-shaped masks selectively into said light delivering optical system and retracting the same from said light delivering optical system so that the longer-side direction of said laser beam may be intercepted partially.

3. The ablation apparatus according to claim 2, wherein said advancing-and-retracting means consists of a rotating means for rotating said each strip-shaped mask respectively.

4. The ablation apparatus according to claim 2, wherein said advancing-and-retracting means consists of a slide means for sliding said each strip shaped mask respectively.

5. The ablation apparatus according to claim 1, wherein said light delivering optical system includes a laser beam source for emitting the laser beam and wherein said object is a cornea.

6. An ablation apparatus comprising:
   light delivering optical system for delivering a laser beam of which a cross section at a perpendicular plane relative to an optical axis is a slender rectangular shape to an object to be ablated;
   beam moving means for moving the laser beam to an intersecting direction relative to the optical axis of said light delivering optical system;
   dividing-and-masking means for dividing selectively a longer-side direction of the laser beam of which a cross section is a rectangular shape and masking the same selectively;
   divided mask moving means for moving said dividing-and-masking means along the longer-side direction of the laser beam;
   data input means for inputting data relating to an ablation area of said object; and
   control means for receiving the data input to said data input means and for controlling the condition masked by said dividing-and-masking means at respective positions of the laser beam moved by said beam moving means and the position moved by said divided mask moving means based on the data inputted by using said data input means, wherein the ablation apparatus ablates convex parts of the object which have a surface roughness.

7. The ablation apparatus according to claim 6, wherein said dividing-and-masking means consists of a large number of strip-shaped masks arranged in a longer-side direction of the laser beam of which a cross section is a rectangular shape, and
   advancing-and-retracting means for advancing said strip shaped masks selectively into said light delivering optical system and retracting the same from said light delivering optical system so that the longer-side direction of said laser beam may be intercepted partially.

8. The ablation apparatus according to claim 7, wherein each of said strip-shaped masks has approximately the same width toward the longer-side direction of the laser beam, and the whole of said strip-shaped masks is configured so as to move along the longer-side direction of the laser beam by said divided mask moving means, whereby the whole of said strip-shaped masks is controlled so that the whole of said strip-shaped masks may move by the amount of the movement less than the width of the mask, apparently.

9. The ablation apparatus according to claim 7, wherein said advancing-and-retracting means consists of a rotating means for rotating said each strip shaped mask respectively.

10. The ablation apparatus according to claim 7, wherein said advancing-and-retracting means consists of a slide means for sliding said each strip shaped mask respectively.

11. The ablation apparatus according to claim 7, wherein said control means controls the mask position moved by said divided mask moving means with defining one scan of the laser beam as a unit relative to said object to be ablated.

12. The ablation apparatus according to claim 6, wherein said light delivering optical system includes a laser beam source for emitting the laser beam and wherein said object is a cornea.

13. An ablation apparatus comprising:

light delivering optical system for delivering such a laser beam of which a cross section is a slender rectangular shape that has an approximate uniform intensity distribution of the beam in one direction, and a Gaussian distribution in another direction, to an object to be ablated;

beam moving means for moving the laser beam to the direction of Gaussian distribution of said beam relative to the optical axis of said light delivering optical system;

dividing-and-masking means for dividing selectively a longer-side direction of the laser beam of which a cross section is a rectangular shape and masking the same selectively;

data input means for inputting data relating to an ablation area of said object; and control means for receiving the data input to said data input means and for controlling the condition masked by said dividing-and-masking means at respective positions of the laser beam moved by said beam moving means based on the data inputted by using said data input means, wherein the ablation apparatus ablates convex parts of the object which have a surface roughness.

14. The ablation apparatus according to claim 13, wherein said light delivering optical system includes a laser beam source for emitting the laser beam and wherein said laser beam is a pulse wave, and said beam moving means is moved under the condition that is synchronized with the pulse wave.

15. The ablation apparatus according to claim 13, wherein said dividing-and-masking means has a large number of strip-shaped masks arranged in a longer-side direction of the laser beam of which a cross section is a rectangular shape; and advancing-and-retracting means for advancing said strip-shaped masks selectively into said light delivering optical system and retracting the same from said light delivering optical system so that the longer-side direction of said laser beam may be intercepted partially.

16. The ablation apparatus according to claim 15, wherein said advancing-and-retracting means consists of a rotating means for rotating said each strip-shaped mask respectively.

17. The ablation apparatus according to claim 15, wherein said advancing-and-retracting means consists of a slide means for sliding said each strip-shaped mask respectively.

18. The ablation apparatus according to claim 13, wherein light delivering optical system includes a laser beam source for emitting the laser beam and wherein said object is a cornea.

19. The ablation apparatus according to claim 13, further comprising:

an image rotator for rotating the laser beam on the optical axis in said light delivering optical system; and an aperture with a variable diameter for restricting the ablation area.

* * * * *